US012605558B2

(12) United States Patent
Uchida et al.

(10) Patent No.: US 12,605,558 B2
(45) Date of Patent: Apr. 21, 2026

(54) AUTOMATED EXTERNAL DEFIBRILLATOR

(71) Applicant: Nihon Kohden Corporation, Tokyo (JP)

(72) Inventors: Takahiro Uchida, Saitama (JP); Fumihito Iwai, Saitama (JP); Naoto Akiyama, Saitama (JP); Ryosuke Kuno, Saitama (JP); Yuji Igawa, Saitama (JP)

(73) Assignee: Nihon Kohden Corporation, Tokyo (JP)

( * ) Notice: Subject to any disclaimer, the term of this patent is extended or adjusted under 35 U.S.C. 154(b) by 497 days.

(21) Appl. No.: 18/007,831

(22) PCT Filed: Jun. 7, 2021

(86) PCT No.: PCT/JP2021/021590
§ 371 (c)(1),
(2) Date: Dec. 2, 2022

(87) PCT Pub. No.: WO2021/256315
PCT Pub. Date: Dec. 23, 2021

(65) Prior Publication Data
US 2023/0226364 A1     Jul. 20, 2023

(30) Foreign Application Priority Data
Jun. 17, 2020     (JP) ................................. 2020-104692

(51) Int. Cl.
*A61N 1/39*          (2006.01)
(52) U.S. Cl.
CPC .................................. *A61N 1/3904* (2017.08)

(58) Field of Classification Search
CPC .................................................... A61N 1/3904
See application file for complete search history.

(56) References Cited

U.S. PATENT DOCUMENTS

| | | |
|---|---|---|
| 5,897,576 A | 4/1999 | Olson et al. |
| 5,955,956 A | 9/1999 | Stendahl et al. |
| 5,983,137 A | 11/1999 | Yerkovich |
| 2011/0046688 A1 | 2/2011 | Schwibner et al. |
| 2011/0130799 A1 | 6/2011 | Kubat et al. |
| 2015/0100102 A1 | 4/2015 | Kubat et al. |

(Continued)

FOREIGN PATENT DOCUMENTS

| | | |
|---|---|---|
| JP | 2001516122 A | 9/2001 |
| JP | 2015192923 A | 11/2015 |

(Continued)

OTHER PUBLICATIONS

International Search Report and Written Opinion issued in International Application No. PCT/JP2021/021590, issued on Sep. 23, 2021, 9 pages.

(Continued)

*Primary Examiner* — Joseph M Dietrich
(74) *Attorney, Agent, or Firm* — Dorsey & Whitney LLP

(57)          ABSTRACT

An automated external defibrillator (AED) includes: a battery configured to supply electric power to the AED; an indicator configured to visually provide predetermined information related to the AED and a remaining level of the battery; and an indicator controller configured to change a visual aspect of the indicator according to the remaining level.

7 Claims, 4 Drawing Sheets

(56) References Cited

U.S. PATENT DOCUMENTS

2019/0111247 A1*  4/2019  Zhao ................... A61N 1/3925
2022/0312680 A1  10/2022  Nii

FOREIGN PATENT DOCUMENTS

JP        6695486 B1    4/2020
WO        9844989 A1   10/1998
WO     2021256315 A1   12/2021

OTHER PUBLICATIONS

Office Action issued in Japanese Patent Application No. 2020-104692, issued on Dec. 19, 2023, 5 pages, including 3 pages of English translation.

* cited by examiner

AUTOMATED EXTERNAL DEFIBRILLATOR

This application claims priority under 35 U.S.C. § 371 to International Application No. PCT/JP2021/021590, filed Jun. 7, 2021, entitled "AUTOMATED EXTERNAL DEFI-BRILLATOR," which in turn claims priority to Japanese Patent Application No. 2020-104692, filed Jun. 17, 2020, entitled "AUTOMATED EXTERNAL DEFIBRILLATOR", each of which is incorporated by reference herein, in the entirety and for all purposes.

TECHNICAL FIELD

The present disclosure relates to an automated external defibrillator.

BACKGROUND ART

Recently, automated external defibrillators (hereinafter abbreviated to AEDs) are rapidly spreading. Such an AED gives a strong electric shock for defibrillation to a heart of a patient who has undergone sudden cardiac arrest due to ventricular fibrillation, to thereby restore a function of the heart of the patient. The AED is mounted with a battery as a power supply. In order to manage a remaining level of the battery of the AED, a dedicated indicator for displaying the remaining level of the battery is provided in the AED (e.g. see JP-A-2001-516122).

SUMMARY

With the rapid spread of the AEDs, miniaturization and weight reduction of the AEDs are being currently studied. In this respect, when the number of indicators that are used for providing information and provided in such an AED is increased, usability of the AED is improved. On the other hand, the increase in the number of the indicators causes an increase in the size and the weight of the AED. Thus, there is room to study a reduction in the number of the indicators provided in the AED from the viewpoint of the miniaturization and/or the weight reduction of the AED while maintaining the usability of the AED.

The present disclosure is directed to reducing the number of indicators provided in an AED from a viewpoint of miniaturization and/or weight reduction of the AED while maintaining usability of the AED.

According to one or more aspects of the present disclosure, there is provided an automated external defibrillator. The automated external defibrillator includes: a battery configured to supply electric power to the automated external defibrillator; an indicator configured to visually provide predetermined information related to the automated external defibrillator and a remaining level of the battery; and an indicator controller configured to change a visual aspect of the indicator according to the remaining level.

BRIEF DESCRIPTION OF DRAWINGS

FIG. 4 is a view for explaining a visual aspect of the indicator that can be changed according to a remaining level of a battery.

DESCRIPTION OF EMBODIMENT

An embodiment will be described below with reference to the drawings. Dimensions of each member shown in each drawing may be different from actual dimensions of the member for convenience of explanation.

Figure 1:
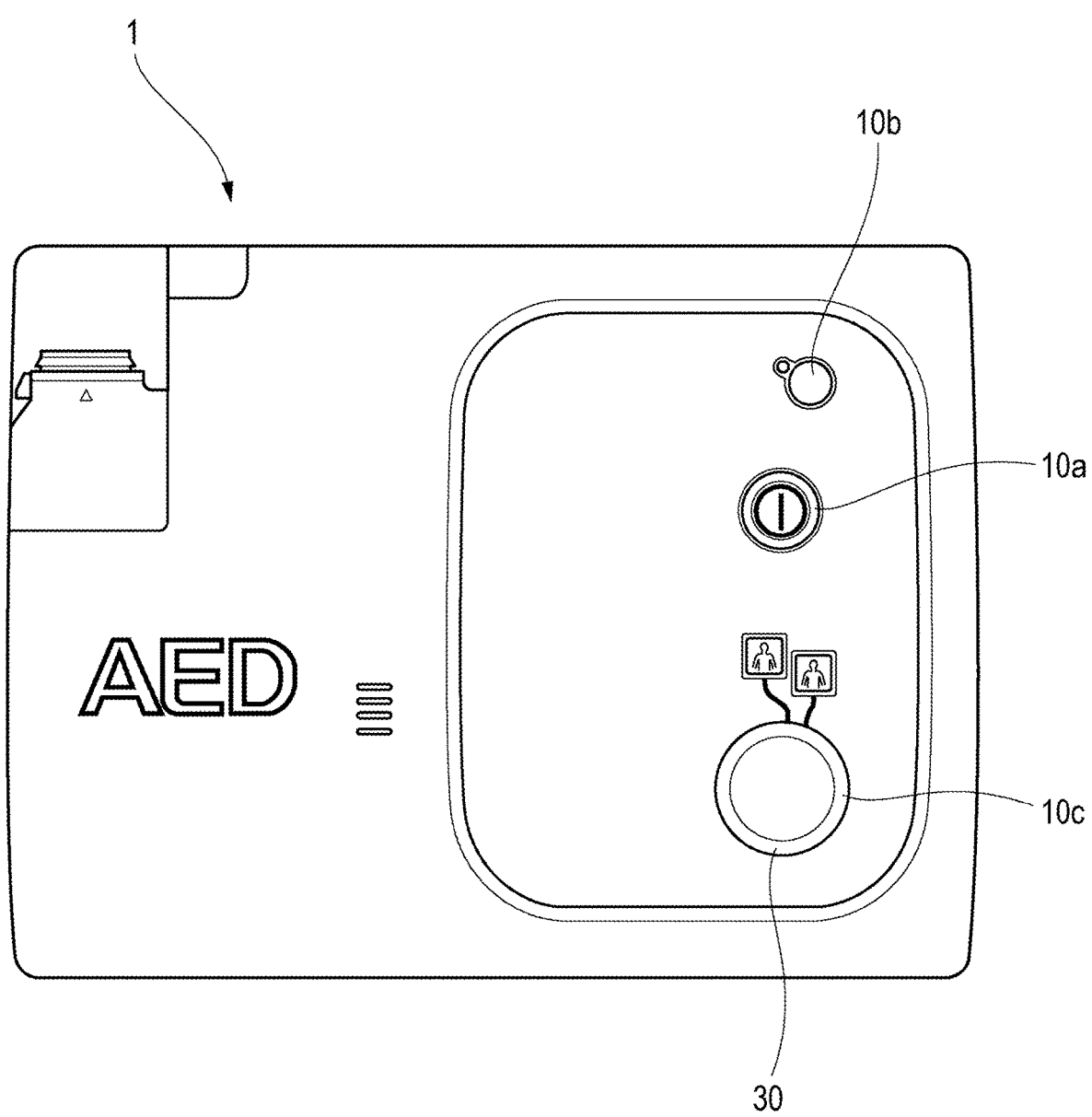
FIG. 1 is a front view of an automated external defibrillator (hereinafter abbreviated to AED) according to an embodiment of the present disclosure (hereinafter referred to as the present embodiment).
Figure 2:
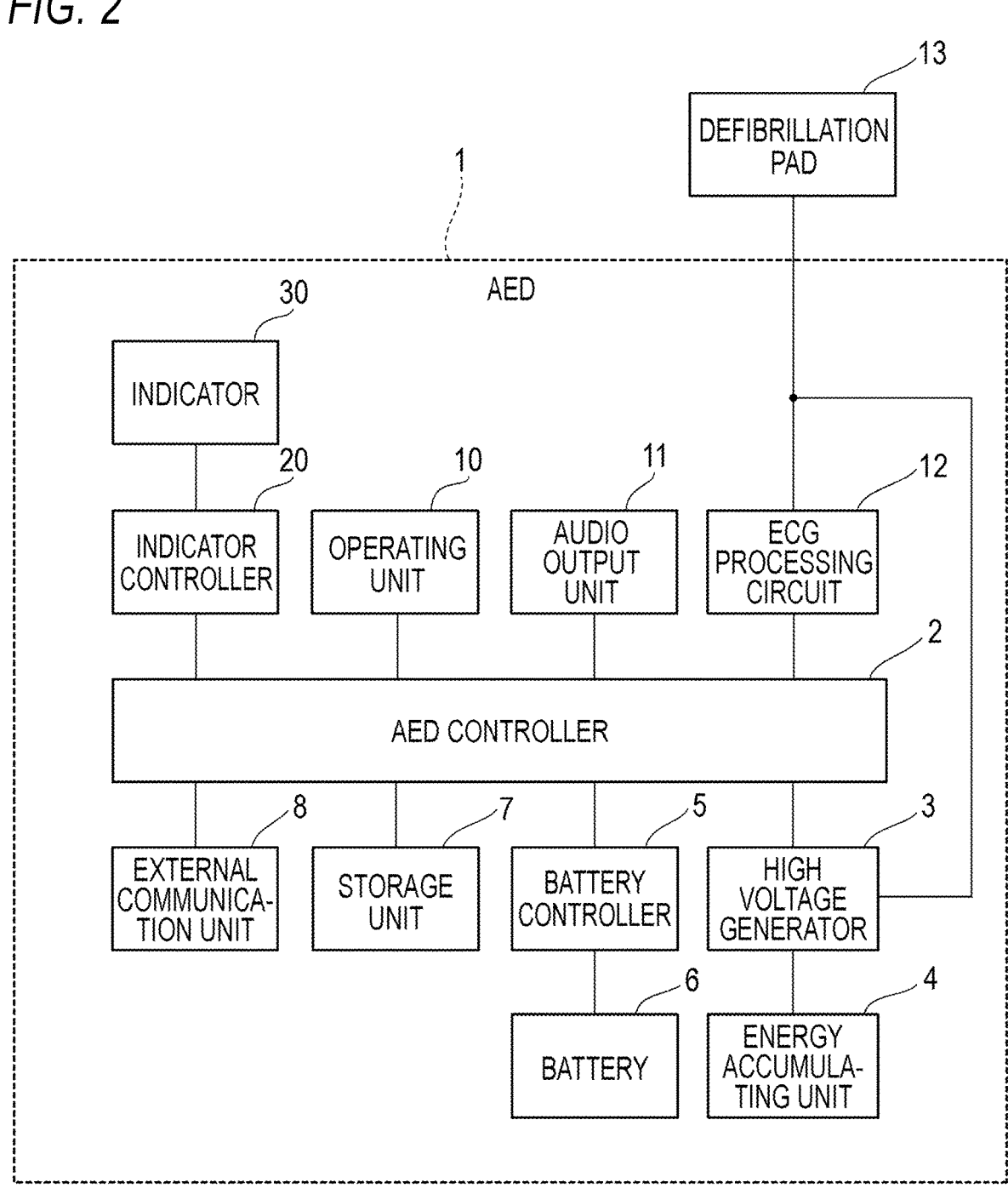
FIG. 2 is a block diagram illustrating a configuration of the AED
Figure 3:
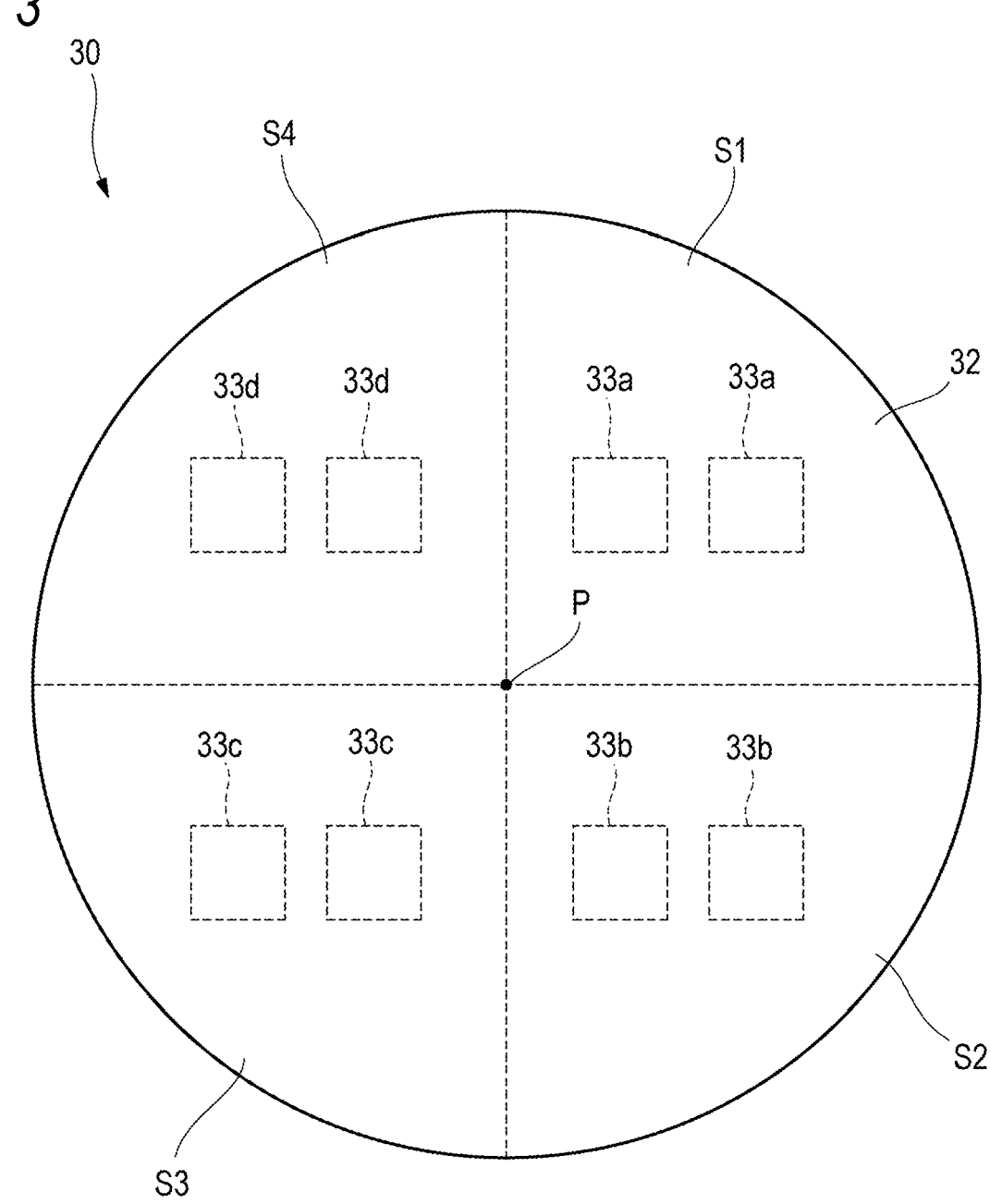
FIG. 3 is a front view schematically illustrating an indicator mounted on a shock button.

First, a configuration of an automated external defibrillator 1 (hereinafter abbreviated to AED 1) will be described below with reference to FIG. 1 to FIG. 3. FIG. 1 is a front view of the AED 1 according to the present embodiment. FIG. 2 is a block diagram illustrating the configuration of the AED 1. FIG. 3 is a front view schematically illustrating an indicator 30 mounted on a shock button 10c.

As shown in FIG. 2, the AED 1 is provided with an AED controller 2, a high voltage generator 3, an energy accumulating unit 4, a battery 6, a battery controller 5, a storage unit 7, and an external communication unit 8. The AED 1 is further provided with an ECG processing circuit 12, an audio output unit 11, an operating unit 10, an indicator controller 20, and the indicator 30.

The AED 1 is a medical device that is configured to give an electric shock to a heart of a patient who has undergone cardiac arrest due to ventricular fibrillation, to thereby restore a function of the heart of the patient. The AED controller 2 is configured to control each of the constituent components provided in the AED 1. The AED controller 2 is, for example, constituted by a microcontroller including a processor and a memory, and an integrated circuit such as an ASIC (Application Specific Integrated Circuit). The processor includes, for example, at least one of a CPU (Central Processing Unit), an MPU (Micro Processing Unit), and a GPU (Graphics Processing Unit). The memory includes an ROM (Read Only Memory) and an RAM (Random Access Memory).

The high voltage generator 3 is configured to charge the energy accumulating unit 4 with electric energy for giving the patient (subject) an electric shock for defibrillation, and to discharge the electric energy accumulated in the energy accumulating unit 4. The energy accumulating unit 4 is configured to accumulate the electric energy for giving the patient the electric shock for defibrillation. For example, the energy accumulating unit 4 may be a high voltage film capacitor constituted by dielectric films.

The battery 6 functions as a power supply configured to supply electric power to the constituent components of the AED 1. For example, the battery 6 is a lithium primary battery. The battery controller 5 is provided with a circuit (such as a switching regulator or a series regulator) configured to convert a voltage of the battery 6 into a voltage required for each of the constituent components of the AED 1. Further, the battery controller 5 is configured to transmit a signal related to a remaining level of the battery 6 to the AED controller 2. In this respect, the battery controller 5 may transmit, to the AED controller 2, a signal indicating the voltage of the battery 6, a signal indicating a current value of the battery 6, or a signal indicating impedance of the battery 6 as a signal related to the remaining level of the battery 6. The AED controller 2 determines the remaining level (between 0% and 100%) of the battery 6 based on the signal related to the remaining level of the battery 6 transmitted from the battery controller 5. Then, the AED controller 2 transmits a lighting control signal indicating the remaining level of the battery 6 to the indicator controller 20. Here, when there is no electric power left in the battery 6, the remaining level is 0%. When the battery 6 is fully charged, the remaining level is 100%. Incidentally, the remaining level of the battery 6 may be represented not by a percentage, but, for example, by one out of five levels.

The storage unit 7 is configured to store various programs for operating the AED 1, audio data, and electrocardiogram data of the patient. The storage unit 7 is, for example, constituted by a flash memory or a hard disk. The external communication unit 8 is configured to transmit various data stored in the storage unit 7 to an external device or receive data from the external device. The external communication unit 8 may be an interface into which a connector of a wired cable such as an LAN cable is inserted, or may be a wireless communication module compatible with wireless communication standards such as Bluetooth (registered trademark) and Wi-Fi (registered trademark). When the external communication unit 8 is the wireless communication module, the external communication unit 8 may include a transmission/reception antenna, a high frequency circuit, and a signal processing circuit.

The ECG processing circuit 12 is configured to process electrocardiogram signals outputted from two defibrillation pads 13 attached to the patient. For example, the ECG processing circuit 12 may have a differential amplifier that amplifies a difference between a potential signal outputted from one of the two defibrillation pads 13 and a potential signal outputted from the other defibrillation pad 13 to thereby generate electrocardiogram data, and an AD converter that converts the electrocardiogram data into digital data. The defibrillation pads 13 are detachably attached to the AED 1.

The audio output unit 11 is a speaker that is configured to output voice guidance or a warning sound related to an operation on the AED 1. The operating unit 10 is configured to accept the operation from an operator. As shown in FIG. 1, the operating unit 10 includes a power button 10a for powering on the AED 1, a check button 10b for checking whether the AED 1 can be used or not, and the shock button 10c for giving an electric shock for defibrillation to the patient.

The indicator controller 20 is, for example, an analog control circuit configured to control turning on/off of the indicator 30. In particular, the indicator controller 20 is configured to control turning on/off of the indicator 30 based on a lighting control signal transmitted from the AED controller 2. For example, the indicator controller 20 may be configured to change a visual aspect of the indicator 30 according to the remaining level of the battery 6 after receiving the lighting control signal indicating the remaining level from the AED controller 2. Further, the indicator controller 20 may be configured to turn on the indicator 30 based on the lighting control signal after receiving, from the AED controller 2, the lighting control signal indicating that the AED 1 is ready to give the patient (subject) an electric shock for defibrillation. In this case, the indicator 30 can visibly provide information (an example of predetermined information) indicating that the AED 1 is ready to give the patient an electric shock for defibrillation.

As shown in FIG. 1, the indicator 30 is mounted on the shock button 10c. In other words, a part of the shock button 10c is constituted by the indicator 30. The indicator 30 is configured to be lit when the AED 1 is ready to give the patient an electric shock for defibrillation. By visually recognizing that the indicator 30 has been lit, the operator of the AED 1 can recognize that the AED 1 is ready to give the patient an electric shock. Therefore, the operator is encouraged to press the shock button 10c, due to the fact that the indicator 30 has been lit.

Further, the indicator 30 is configured to visually provide the remaining level of the battery 6 to the outside when the AED 1 is powered ON. In this respect, the indicator 30 is configured to change the visual aspect according to the remaining level of the battery 6.

As shown in FIG. 3, the indicator 30 has a transparent cover 32 that transmits visible light. The transparent cover 32 constitutes the surface of the shock button 10c that the operator touches. A minute diffusion step for diffusing light emitted from each of light emitting elements 33a to 33d may be formed in the surface of the transparent cover 32. The indicator 30 has four light emitting segments S1 to S4 partitioned along its circumferential direction. In this respect, each of the light emitting segments S1 to S4 has an angular region of 90 degree starting from a center point P of the indicator 30. The light emitting segment S1 includes two light emitting elements 33a. The light emitting segment S2 that is adjacent to the light emitting segments S1 and S3 has two light emitting elements 33b. The light emitting segment S3 that is adjacent to the light emitting segments S2 and S4 has two light emitting elements 33c. The light emitting segment S4 that is adjacent to the light emitting segments S1 and S3 has two light emitting elements 33d. The light emitting elements 33a to 33d are, for example, semiconductor light emitting elements such as LEDs (Light Emitting Diodes). Turning on/off of each of the light emitting elements 33a to 33d is controlled by the indicator controller 20.

Visual Aspect of Indicator According to Remaining Level of Battery

Figure 4:
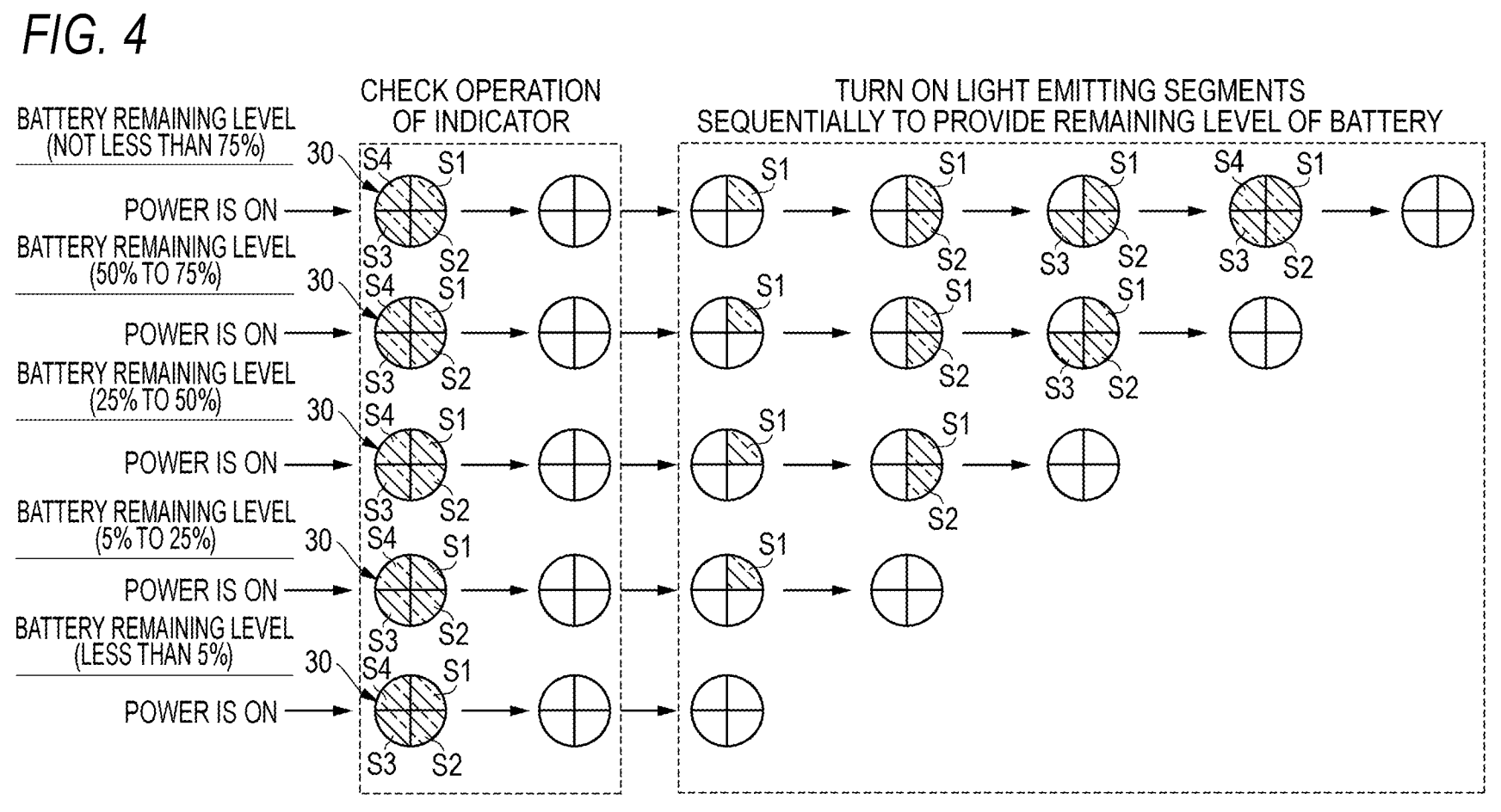

Next, the visual aspect of the indicator 30 that can be changed according to the remaining level of the battery 6 will be described below with reference to FIG. 4. FIG. 4 is a view for explaining the visual aspect of the indicator 30 that can be changed according to the remaining level of the battery 6. In the following description, it is assumed that the indicator controller 20 receives a lighting control signal indicating the remaining level of the battery 6 from the AED controller 2 after the AED 1 is powered ON and before the indicator controller 20 visually provides the remaining level of the battery 6.

Remaining Level of Battery: Not Less than 75%

First, the visual aspect of the indicator 30 will be described when the remaining level of the battery 6 is not less than 75%. As shown in FIG. 4, when the AED 1 is powered ON by an operation made on the power button 10a (see FIG. 1) by the operator, all the light emitting segments S1 to S4 of the indicator 30 are turned on and then turned off in order to check the operation of the indicator 30. Next, in order to present the remaining level of the battery 6 to the operator, the indicator controller 20 turns on the light emitting segment S1 (the two light emitting elements 33a) in a first stage. Next, in a second stage, the indicator controller 20 turns on the light emitting segment S2 (the two light emitting elements 33b) in addition to the light emitting segment S1. In a third stage, the indicator controller 20 turns on the light emitting segment S3 (the two light emitting elements 33c) in addition to the light emitting segments S1 and S2. In a fourth stage, the indicator controller 20 turns on the light emitting segment S4 (the two light emitting elements 33d) in addition to the light emitting segments S1 to S3. In a final stage, the indicator controller 20 turns off all the light emitting segments S1 to S4. Thus, when the remaining level of the battery 6 is not less than 75%, the indicator controller 20 turns on the four light emitting segments S1 to S4 sequentially. A period between the first stage and the final stage is, for example, 1 second.

Remaining Level of Battery: 50% to 75%

Next, the visual aspect of the indicator 30 will be described when the remaining level of the battery 6 is not less than 50% but less than 75%. As shown in FIG. 4, when the AED 1 is powered ON, all the light emitting segments S1 to S4 of the indicator 30 are turned on and then turned off in order to check the operation of the indicator 30. Next, in order to present the remaining level of the battery 6 to the operator, the indicator controller 20 turns on the light emitting segment S1 in a first stage. In a second stage, the indicator controller 20 turns on the light emitting segment S2 in addition to the light emitting segment S1. In a third stage, the indicator controller 20 turns on the light emitting segment S3 in addition to the light emitting segments S1 and S2. In a final stage, the indicator controller 20 turns off the three light emitting segments S1 to S3. Thus, when the remaining level of the battery 6 is not less than 50% but less than 75%, the indicator controller 20 turns on the three light emitting segments S1 to S3 sequentially.

Remaining Level of Battery: 25% to 50%

Next, the visual aspect of the indicator 30 will be described when the remaining level of the battery 6 is not less than 25% but less than 50%. As shown in FIG. 4, when the AED 1 is powered ON, all the light emitting segments S1 to S4 of the indicator 30 are turned on and then turned off in order to check the operation of the indicator 30. Next, in order to report the remaining level of the battery 6 to the operator, the indicator controller 20 turns on the light emitting segment S1 in a first stage. In a second stage, the indicator controller 20 turns on the light emitting segment S2 in addition to the light emitting segment S1. In a final stage, the indicator controller 20 turns off the two light emitting segments S1 and S2. Thus, when the remaining level of the battery 6 is not less than 25% but less than 50%, the indicator controller 20 turns on the two light emitting segments S1 and S2 sequentially.

Remaining Level of Battery: 5% to 25%

Next, the visual aspect of the indicator 30 will be described when the remaining level of the battery 6 is not less than 5% but less than 25%. As shown in FIG. 4, when the AED 1 is powered ON, all the light emitting segments S1 to S4 of the indicator 30 are turned on and then turned off in order to check the operation of the indicator 30. Next, in order to report the remaining level of the battery 6 to the operator, the indicator controller 20 turns on the light emitting segment S1 and then turns off the light emitting segment S1. Thus, when the remaining level of the battery 6 is not less than 5% but less than 25%, the indicator controller 20 turns on only one light emitting segment S1.

Remaining Level of Battery: Less than 5%

Next, the visual aspect of the indicator 30 will be described when the remaining level of the battery 6 is less than 5%. As shown in FIG. 4, when the AED 1 is powered ON, all the light emitting segments S1 to S4 of the indicator 30 are turned on and then turned off in order to check the operation of the indicator 30. Next, in order to report the remaining level of the battery 6 to the operator, the indicator controller 20 turns off all the light emitting segments S1 to S4. Thus, when the remaining level of the battery 6 is less than 5%, the indicator controller 20 turns on none of the light emitting segments S1 to S4.

According to the present embodiment, as described above, the indicator 30 is configured to visually provide both the information indicating that the AED 1 is ready to give the patient an electric shock for defibrillation and the information indicating the remaining level of the battery 6. Thus, a dedicated indicator for visually providing only the remaining level of the battery 6 does not need to be provided in the AED 1. Accordingly, the number of indicators 30 provided in the AED 1 can be reduced from a viewpoint of miniaturization and weight reduction of the AED 1 while usability of the AED 1 is maintained. Further, when the AED 1 is powered ON, the remaining level of the battery 6 is provided by the indicator 30, so that the operator of the AED 1 can easily notice the remaining level of the battery 6. In particular, the operator can grasp the remaining level of the battery 6 before use. Therefore, the operator can use the AED 1 more surely.

Further, in the present embodiment, the indicator controller 20 is configured to increase the number of the light emitting segments to be turned on sequentially during a predetermined period (e.g. 1 second) as the remaining level of the battery 6 increases. Specifically, when the remaining level is not less than 75%, all the four light emitting segments are turned on sequentially. When the remaining level is not less than 50% but less than 75%, three of the light emitting segments are turned on sequentially. When the remaining level is not less than 25% but less than 50%, two of the light emitting segments are turned on sequentially. When the remaining level is not less than 5% but less than 25%, only one of the light emitting segments is turned on. When the remaining level is less than 5%, none of the light emitting segments is turned on.

Thus, by visually recognizing the number of the light emitting segments S1 to S4 that have been turned on sequentially along the circumferential direction of the indicator 30, the operator of the AED 1 can intuitively grasp the remaining level of the battery 6.

Further, in the present embodiment, the indicator controller 20 turns on all of the light emitting segments S1 to S4 after the AED 1 is powered ON and before the indicator 30 visually provides the remaining level of the battery 6. Therefore, by visually recognizing that all the light emitting segments S1 to S4 have been turned on, the operator can recognize that the light emitting segments S1 to S4 are operating normally. In this respect, the operator can recognize that the indicator 30 can correctly provide the remaining level of the battery 6, due to the fact that all the light emitting segments S1 to S4 have been turned on.

Moreover, in the present embodiment, the indicator 30 is mounted on the shock button 10c. That is, since the indicator 30 and the shock button 10c are integrally configured, the size and the weight of the AED 1 can be reduced. Further, the operator is guided to press the shock button 10c, due to the fact that the indicator 30 has been lit. Therefore, the operator can press the shock button 10c surely.

Although the embodiment of the present disclosure has been described above, the technical scope of the present disclosure should not be interpreted limitedly by the description of the present embodiment. The present embodiment is merely exemplar, and it is going to be understood by those skilled in the art that various changes can be made on the embodiment within the scope of the disclosure described in the scope of claims. The technical scope of the present disclosure should be determined based on the scope of the disclosure described in the scope of claims and the scopes of equivalents thereof.

In the present embodiment, the indicator controller 20 sequentially turns on the light emitting segments according to the remaining level of the battery 6. However, the present embodiment is not limited thereto. For example, the indicator controller 20 may change the number of the light emitting segments to be turned on simultaneously according to the remaining level of the battery 6.

For example, when the remaining level of the battery 6 is not less than 75%, the indicator controller 20 may simultaneously turn on the four light emitting segments S1 to S4 in order to provide the remaining level of the battery 6 to the outside, and then turn off the four light emitting segments S1 to S4. When the remaining level of the battery 6 is not less than 50% but less than 75%, the indicator controller 20 may simultaneously turn on the three light emitting segments S1 to S3 in order to provide the remaining level of the battery 6 to the outside, and then turn off the three light emitting segments S1 to S3. When the remaining level of the battery 6 is not less than 25% but less than 50%, the indicator controller 20 may simultaneously turn on the two light emitting segments S1 and S2 in order to provide the remaining level of the battery 6 to the outside, and then turn off the two light emitting segments S1 and S2.

Further, the indicator controller 20 increases the number of the light emitting segments to be turned on sequentially as the remaining level of the battery 6 increases. However, the present embodiment is not limited thereto. For example, the indicator controller 20 may reduce the number of the light emitting segments to be turned on sequentially as the remaining level of the battery 6 increases.

In this case, when the remaining level is not less than 75%, none of the light emitting segment is turned on. When the remaining level is not less than 50% but less than 75%, only one of the light emitting segments is turned on. When the remaining level is not less than 25% but less than 50%, two of the light emitting segments are turned on sequentially. When the remaining level is not less than 5% but less than 25%, three of the light emitting segments are turned on sequentially. When the remaining level is less than 5%, the four light emitting segments are turned on sequentially.

Further, the indicator controller 20 increases the number of the light emitting segments to be turned on sequentially in each stage. However, the present embodiment is not limited thereto. For example, the indicator controller 20 may reduce the number of the light emitting segments to be turned on sequentially in each stage.

Description will be made, for example, in the case where the remaining level of the battery 6 is not less than 75%. In this case, all the light emitting segments S1 to S4 are turned on in a first stage. Next, the light emitting segments S1 to S3 are turned on in a second stage. The light emitting segments S1 and S2 are turned on in a third stage. The light emitting segment S1 is turned on in a fourth stage. All the light emitting segments S1 to S4 are turned off in a final stage.

Further, the indicator controller 20 may change the position of the light emitting segment that should be turned on in each stage.

Description will be made, for example, in the case where the remaining level of the battery 6 is not less than 75%. In this case, the light emitting segment S1 is turned on and then turned off in a first stage. Next, the light emitting segment S2 is turned on and then turned off in a second stage. The light emitting segment S3 is turned on and then turned off in a third stage. The light emitting segment S4 is turned on and then turned off in a fourth stage. All the light emitting segments are turned off in a final stage. Thus, the position of the light emitting segment that should be turned on may be changed in each stage.

Further, the indicator controller 20 changes the number of the light emitting segments S1 to S4 that should be turned on sequentially (that is, lighting areas of the indicator 30) as an example of the visual aspect of the indicator 30 according to the remaining level of the battery 6. However, the present embodiment is not limited thereto.

For example, the indicator controller 20 may change a lighting time, brightness, the number of times of blinking, a lighting color, etc. of the indicator 30 as the visual aspect of the indicator 30 according to the remaining level of the battery 6. Specifically, the lighting time of the indicator 30 after the power is ON may lengthen as the remaining level of the battery 6 increases. Further, the brightness of the light emitted from the indicator 30 may increase as the remaining level of the battery 6 increases. Further, the number of times of blinking of the indicator 30 may increase as the remaining level of the battery 6 increases. Further, the indicator 30 may emit light in a different color to the outside according to the remaining level of the battery 6. In this case, three light emitting elements (a red LED, a blue LED and a green LED) may be disposed in each of the light emitting segments S1 to S4.

Further, in the present embodiment, the indicator 30 visually provides the remaining level of the battery 6 when the AED 1 is powered ON. However, the present embodiment is not limited thereto. For example, the indicator 30 may visually provide the remaining level of the battery 6 at every predetermined time interval (e.g. hourly). Further, the indicator 30 may visually provide the remaining level of the battery 6 when the check button 10b is operated by the operator. Further, the indicator 30 may visually provide the remaining level of the battery 6 when the AED 1 is powered OFF or when the battery 6 is attached to the AED 1.

Further, in the present embodiment, the indicator 30 is mounted on the shock button 10c. However, the present embodiment is not limited thereto. For example, the indicator 30 may be mounted on the power button 10a or the check button 10b. In this case, the transparent cover of the indicator 30 constitutes the surface of the power button or the surface of the check button. Further, the aforementioned battery remaining level reporting mechanism may be incorporated into another not-shown indicator (such as an indicator for reporting any error).

For example, when the indicator 30 is mounted on the check button 10b, the indicator 30 can visually provide both information indicating that the AED 1 is executing self-check and the remaining level of the battery 6. In particular, by blinking the light emitting segments of the indicator 30, the information indicating that the AED 1 is executing self-check (an example of the predetermined information) can be presented to the outside.

Further, in the present embodiment, two light emitting elements are provided in each of the light emitting segments. However, the number of the light emitting elements provided in the light emitting segment is not limited particularly. For example, one light emitting element or three or more light emitting elements may be provided in the light emitting segment. Further, the indicator 30 is partitioned into the four light emitting segments S1 to S4. However, the number of the partitioned light emitting segments is not limited particularly. Further, in the present embodiment, the remaining level of the battery 6 is divided into five levels. However, the number of the divided levels for indicating the remaining level of the battery 6 is not limited particularly. For example, the remaining level of the battery 6 may be divided into six or more levels. When, for example, the remaining level of the battery 6 is divided into ten levels, the operator can grasp the remaining level of the battery 6 in increments of 10%.

This application is based on Japanese Patent Application No. 2020-104692 filed on Jun. 17, 2020, the entire contents of which are incorporated herein by reference.

The invention claimed is:

1. An automated external defibrillator comprising:
a battery configured to supply electric power to the automated external defibrillator;
a single indicator configured to visually provide information indicating that the automated external defibrillator is ready to give a subject an electric shock for defibrillation and a remaining level of the battery; and
an indicator controller configured to change a visual aspect of the indicator according to the remaining level, and configured to turn on the indicator when the automated external defibrillator is ready to give the subject the electric shock.

2. The automated external defibrillator according to claim 1, wherein
the indicator is configured to visually provide the remaining level when the automated external defibrillator is powered ON.

3. An automated external defibrillator comprising:
a battery configured to supply electric power to the automated external defibrillator;
an indicator configured to visually provide predetermined information related to the automated external defibrillator and a remaining level of the battery; and
an indicator controller configured to change a visual aspect of the indicator according to the remaining level,
wherein the indicator comprises light emitting segments,
each of the light emitting segments comprises at least one light emitting element,
the indicator controller is configured control turning on/off of the light emitting segments according to the remaining level, and the indicator controller is configured to turn on all the light emitting segments after the automated external defibrillator is powered ON and before the indicator visually provides the remaining level.

4. The automated external defibrillator according to claim 3, wherein
the indicator controller is configured to increase a number of the light emitting segments to be turned on as the remaining level increases.

5. The automated external defibrillator according to claim 4, wherein
the indicator controller is configured to increase the number of the light emitting segments to be turned on sequentially as the remaining level increases.

6. The automated external defibrillator according to claim 3, wherein
the light emitting segments are disposed along a circumferential direction of the indicator, and
the indicator controller is configured to sequentially turn on the light emitting segments along the circumferential direction.

7. An automated external defibrillator comprising:
a battery configured to supply electric power to the automated external defibrillator;
an indicator configured to visually provide predetermined information related to the automated external defibrillator and a remaining level of the battery; and
an indicator controller configured to change a visual aspect of the indicator according to the remaining level,
wherein the indicator is integrally configured with a shock button for giving an electric shock for defibrillation to a subject.

* * * * *